Figure 1:
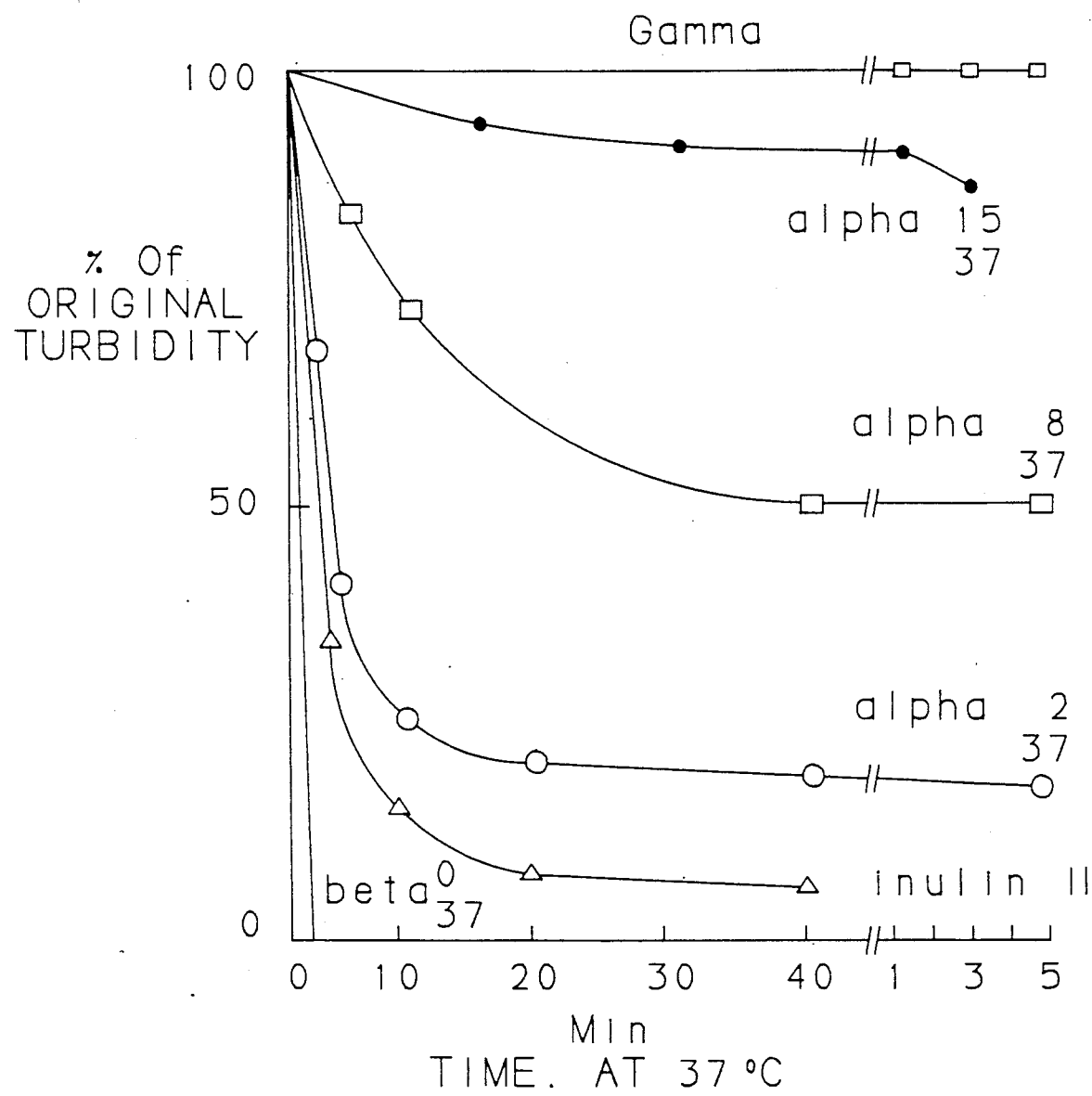

United States Patent [19]

Cooper

[11] Patent Number: 5,051,408

[45] Date of Patent: Sep. 24, 1991

[54] INULIN COMPOSITIONS IN GAMMA POLYMORPHIC FORM

[75] Inventor: Peter Dodd Cooper, Monash, Australia

[73] Assignee: The Australian National University, Acton, Australia

[21] Appl. No.: 501,752

[22] Filed: Mar. 30, 1990

Related U.S. Application Data

[63] Continuation of Ser. No. 86,634, Aug. 3, 1987, Pat. No. 4,954,622.

[30] Foreign Application Priority Data

Oct. 31, 1985 [AU] Australia .............................. PH3187

[51] Int. Cl.$^5$ .................. A61K 31/715; A61K 39/02; A01N 65/00; C08B 37/18
[52] U.S. Cl. ..................................... 514/54; 514/885; 424/92; 424/93; 536/4.1; 536/1.1; 536/123; 536/127
[58] Field of Search ................. 536/127, 4.1, 123, 1.1; 514/54, 885; 424/92, 93

[56] References Cited

PUBLICATIONS

Phelps; Biochem. J. 95:41–47 (1965).

Sommerman et al.; Biochem. Biophys. Res. Commun. 122(1):319–324 (1984).
Cooper et al.; Molecular Immunology 23(8):895–901 (1986).
Cooper et al.; Molecular Immunology 23(8):903–908 (1986).
Cooper et al.; Int. J. Cancer 33:683–687 (1984).
Cooper; Advances in Immunity and Cancer Therapy vol. 1 Ed. Ray; pp. 125–166 Chap. 4 (Sep. 1985).

*Primary Examiner*—Johnnie R. Brown
*Assistant Examiner*—Nancy S. Carson
*Attorney, Agent, or Firm*—Bacon & Thomas

[57] ABSTRACT

A process for preparing gamma inulin comprising the steps of (a) recrystallizing crude inulin from water at a temperature below 37° C. to obtain a suspension, (b) heating the suspension at a temperature of from about 25° to 45° C. for about 1–3 days, (c) further heating the suspension at a temperature of about 40° to 55° C. for about 0.5 to 1.5 hours, and (d) isolating insoluble gamma inulin from the suspension. A composition comprising particles of inulin or an inulin derivative in the gamma polymorphic form is characterized in that the particles have a low rate of solution in aqueous media above 30° C., particularly above 37° C. The composition is effective as the active component of an immunotherapeutic preparation for activation of the alternative pathway of complement, or for antitumor treatment.

16 Claims, 5 Drawing Sheets

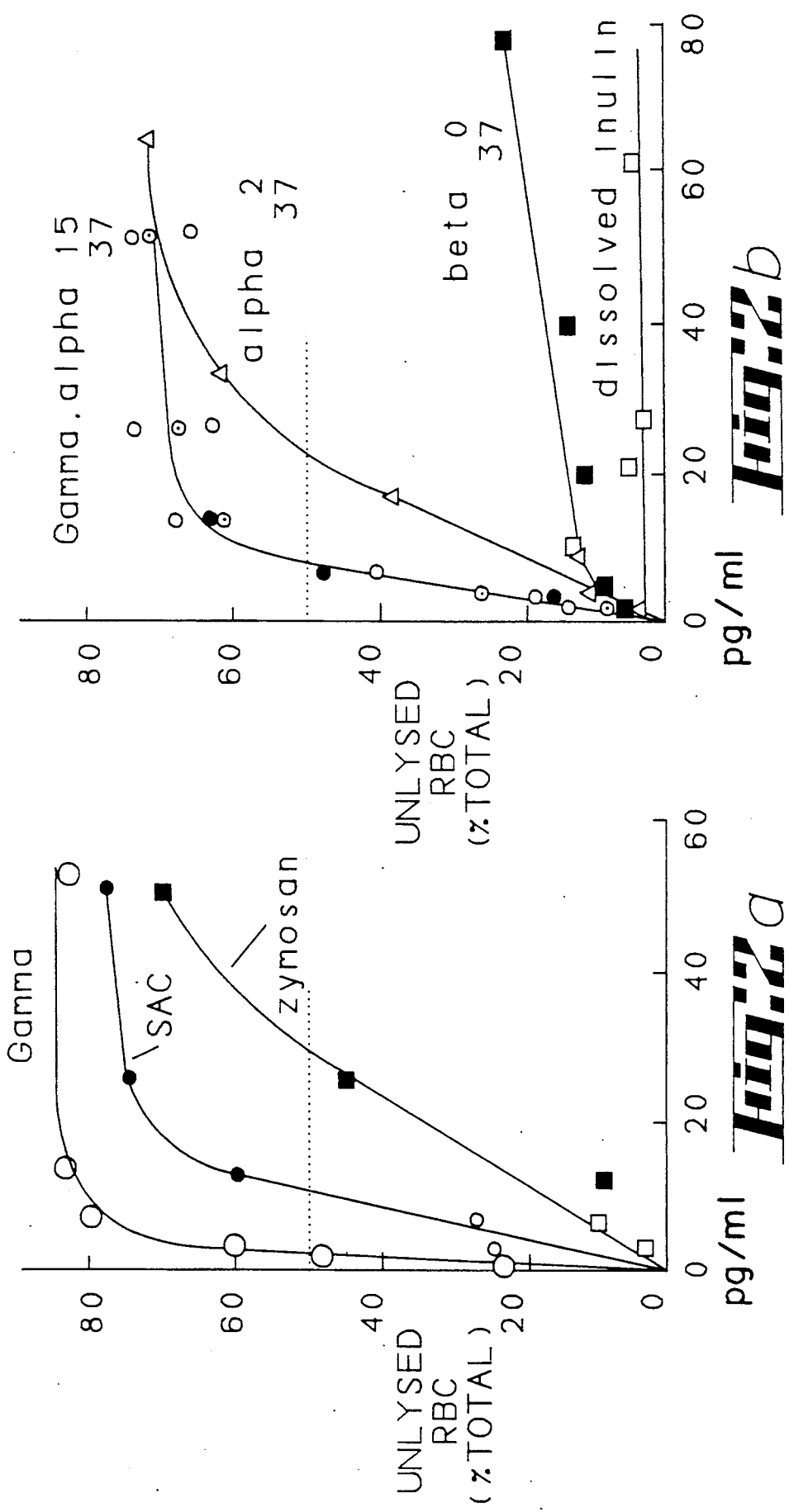

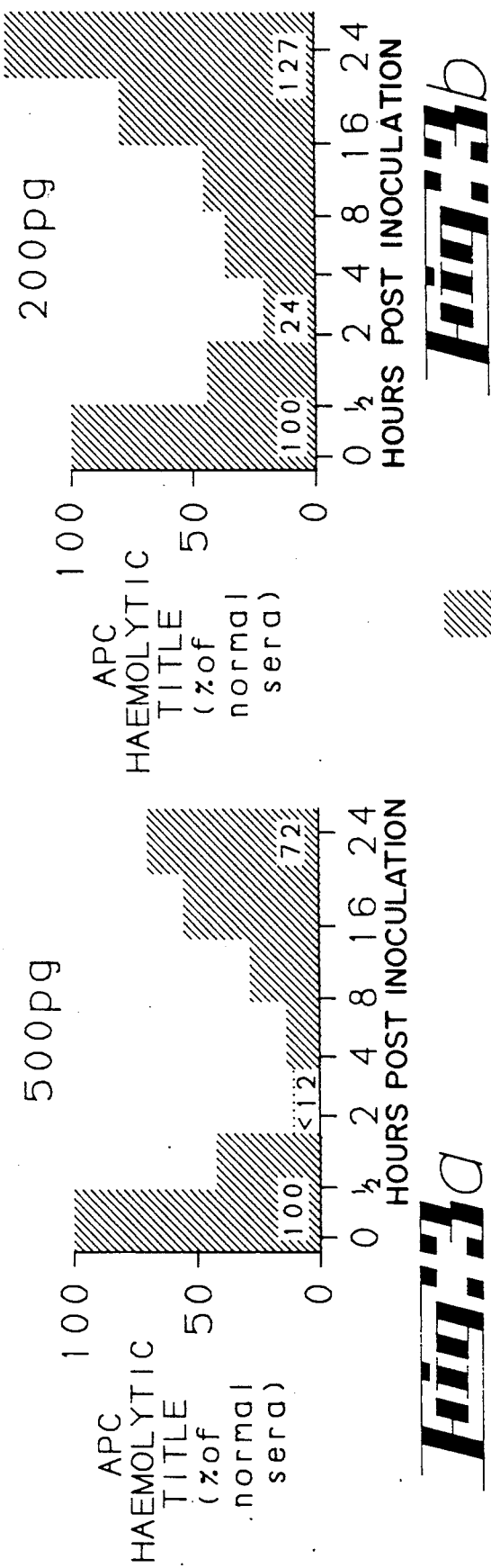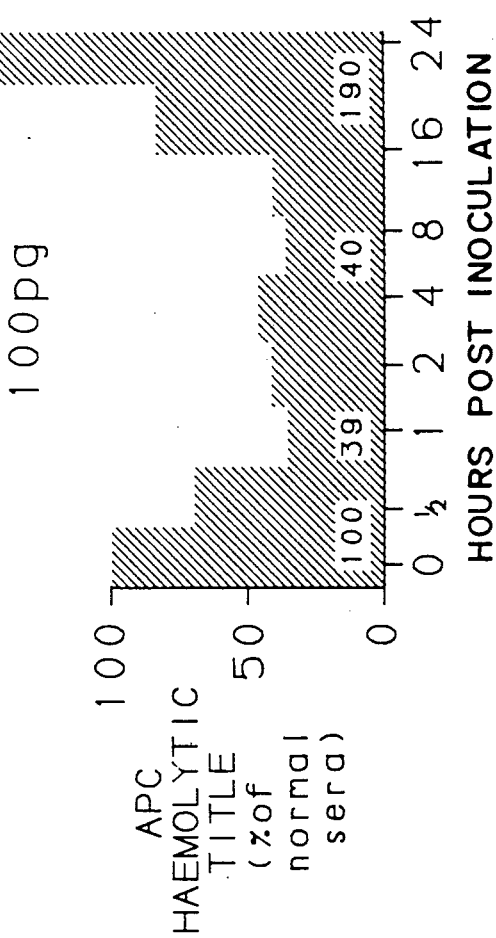

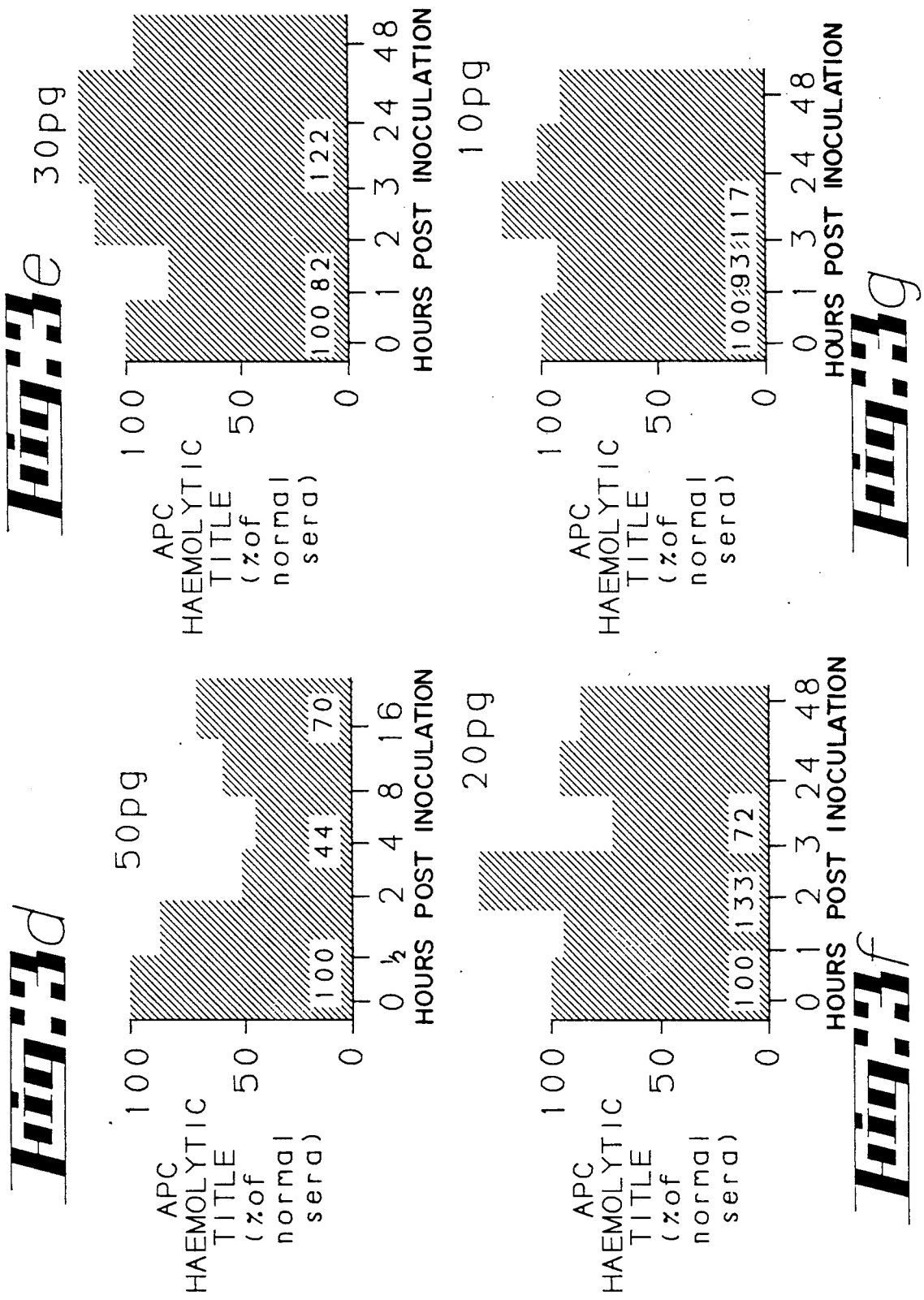

INULIN COMPOSITIONS IN GAMMA POLYMORPHIC FORM

This application is a continuation of application Ser. No. 086,634, filed Aug. 3, 1987, now allowed, and issued as U.S. Pat. No. 4,954,622.

This invention relates to the preparation and identification of individual polymorphic crystalline forms of inulin, immunotherapeutic preparations containing inulin and to a method of antitumour treatment by the administration of those preparations in which inulin is in an insoluble or particulate form.

"Inulin" is a simple, inert polysaccharide comprising a family of linear $\beta$-D-(2→1) polyfructofuranosyl $\alpha$-D-glucoses, in which an unbranched chain of up to 100 fructose moieties is linked to a single terminal glucose, the end fructose-glucose pair incidentally being identical to sucrose; there are no other components. Inulin preparations are therefore molecularly polydisperse (mol. wts up to 16,000), neutral polysaccharides of simple, known composition. Inulin is the storage carbohydrate of Compositae and is cheaply available from dahlia tubers. It has a relatively hydrophobic, polyoxyethylene-like backbone, and this unusual structure plus its non-ionised nature allows recrystallisation and easy preparation in a very pure state.

Although the molecular composition of inulin is well-known, the reported determinations of its solubility are conflicting. For example, the Merck Index describes inulin as "slightly soluble in cold water, soluble in hot", whereas a quantitative study (Biochem. J., 1965, 95, 41-47) suggests that two distinct forms of inulin exist—the first obtained by precipitation from water, the second by precipitation from ethanol—both of which are substantially soluble in water at 37° C. It is also known that suspensions of inulin become less soluble on standing. The form obtained from precipitation from water is referred to as alpha-inulin, and the form obtained by precipitation from ethanol is known as beta-inulin. However, the conformational differences between the two forms have not been determined, nor has a method been established which can distinguish between the various polymorphic forms of inulin.

In developing a method for distinguishing the various forms of inulin, a third, hitherto unknown, polymorph has been discovered and isolated.

This third polymorph, hereinafter referred to as gamma-inulin, is virtually insoluble in water at 37° C., but is soluble at temperatures in the range of 70°-80° C., as are the alpha and beta forms. The series of polymorphic forms in which inulin crystallises may be characterised by their different solubility rates in aqueous media ranging from one instantly soluble at 23° C. (beta $_{23}{}^{0}$ inulin) through a form soluble at 37° C. with a half-time of 8 minutes (alpha $_{37}{}^{8}$ inulin) to a form virtually insoluble at 37° C. (gamma inulin). All forms are interconvertible, the more soluble and unstable progressing on standing to less soluble and more stable forms, only reversible by complete solution followed by recystallisation. The end product is the stable gamma inulin.

According to the present invention, there is provided, a composition comprising particles of inulin or an inulin derivative in the gamma polymorphic form, characterised in that said particles have a low rate of solution in aqueous media above 30° C.

The active components which may be used in accordance with this invention include not only inulin, $\beta$-D-[2-1]-polyfructofuranosyl $\alpha$-D-glucose, but also derivatives thereof including $\beta$-D-[2-1] polyfructose which may be obtained by enzymatic removal of the end glucose from inulin, for example using an invertase or inulase enzyme capable of removing this end glucose. Other derivatives included within the ambit of this invention are derivatives of inulin in which the free hydroxyl groups have been etherified or esterified, for example by chemical substitution with alkyl, aryl or acyl groups by known methods.

The active component is preferably of molecular weight greater than about 3000, more preferably, greater than about 8000.

According to one preferred aspect of the present invention, the composition comprises particles of gamma inulin, which is characterised in that:
(a) its molecular weight is in the range of from about 8,000 to about 16,000; and
(b) it is virtually insoluble in water at 37° C.

In one particularly preferred aspect, this invention provides a composition comprising gamma inulin as described above in a stable, very pure suspension of particles <1 μm in diameter. Such a suspension has been found to be a reagent specific for in vivo and in vitro activation of the alternative pathway of complement (APC) as described in detail below.

It is envisaged that those inulins or inulin derivatives whose molecular weights are too low to convert to the gamma form may be rendered less soluble, and therefore easier to prepare in insoluble crystals, by appropriate chemical substitution, for example by substitution with alkyl, aryl or acyl groupings.

The present invention also provides a process for the preparation of gamma inulin from any convenient source such as commercially available inulin.

Broadly speaking, the process comprises the steps of:
1. removing trace impurities;
2. recrystallising from water (preferably at alkaline pH) at a temperature well below 37° C. to obtain a finely divided particulate in suspension;
3. heating said suspension at a temperature in the range of from about 25° to 45° C. for approximately 1 to 3 days;
4. further heating said suspension at a temperature in the range of from about 40° to 55° C. for approximately 0.5 to 1.5 hours; and
5. isolating the thus-formed insoluble gamma inulin from the suspension.

The following steps comprise a purification procedure for the production of endotoxin(ET)-free "gamma inulin for injection":
1. Inulin powder (obtained, for example, from commercial sources) is first treated to remove trace impurities. This is achieved by washing by suspension in water and resedimentation, recrystallisation from water with minimal heat (preferably less than 70° C.) and cooling or freeze/thawing, and passing in the dissolved state through ion-exchangers such as DEAE-cellulose and sulphonated polystyrene resin. The pH is preferably kept above 6.5. The solution is then sterilised and freedom from endotoxin completed by filtration through an appropriate filter (for example, Zetapor 0.2 μm SP grade charge-modified nylon 66 membrane).
2. The solution is converted to a finely divided precipitate (particles preferably less than 1 μm diameter) of a soluble inulin (mainly alpha form) by recrystallisation at a temperature well below 37° C., preferably 5°

C., and preferably at a high pH (for example, by using a 0.1% ammonia solution) and a concentration preferably greater than 50 mg/ml inulin. After several days, usually 5-7 days, most of the inulin has crystallised.

3. The suspension is then heated to a higher temperature, preferably in the range from 30° to 40° C. for a further period of approximately 1-3 days, when most of the inulin precipitate has converted to the gamma form.

4. The suspension is then further heated for a shorter period of approximately 1 hr at a higher temperature, preferably in the range from 45° to 50° C., to complete the conversion and to dissolve any alpha inulin incapable of conversion.

5. The suspension may be largely freed of soluble matter by sedimentation and resuspension in water.

The suspension is then resuspended to a standard concentration, for example, 62.5 mg solid inulin/ml, which yields 50 mg/ml isotonic saline when mixed with one-quarter vol. 4% w/v saline solution. Concentrations may be measured with a refractometer. The degree of dispersion is checked by appropriate procedures, for example, density gradient centrifugation or electron microscopy.

At all steps after stage 1 described above, endotoxin-free materials and full aseptic techniques are employed. The suspension may be adjusted to isotonicity with saline solution before or after standing at 5° C. Apart from some slight hydrolysis, it is stable up to 45° C. but is preferably not heated further. After freezing and thawing the suspension is still active but the particles may become aggregated.

Earlier research suggests that there exists some fundamental immune principle potentially exploitable for cancer therapy. Unfortunately, the role of the immune system in the genesis/elimination of cancer is not fully understood and remains an area of considerable controversy and doubt. There are many factors involved and the current understanding of the mechanism of action of the immune system on tumours at the cellular level is poor.

From a study of virtually all of the known immunopotentiating agents (approximately 20 compounds) with well substantiated antitumour activity (Cooper, P. D., *Advances in Immunology and Cancer Therapy*, Vol.1, Chapt.4, pp125-166 (1985), Ray, P. K. (Ed.), Springer-Verlag, N.Y.), it has been shown that they either activate the alternative pathway of complement, or they activate macrophages (apparently through their endogenous APC), or both. Thus, despite the great chemical diversity in the molecular structure of these compounds exhibiting antitumour activity, APC activation appears to be a common property. Further, it has been shown that two purified agents which are highly specific for APC activation (i.e., where cytotoxicity and other factors could be ruled out) have significant anti-tumour activity in carefully controlled experiments with specific strains of mice. These two agents were isolated complement component C3b and isolated cobra venom factor (Cooper, P. D. and Sim, R. B., *Int.J.Cancer*, 33, 683-687 (1984)). From this earlier research, it was concluded that other specific APC activators might also be expected to show antitumour activity.

Accordingly, an object of the present invention is the provision of a preparation which, when administered to a patient suffering from cancer, will affect the alternative pathway of complement to reproducibly and significantly increase the survival time, or improve the quality of life, of that patient.

Another object is the provision of a preparation which, when administered to ostensibly healthy persons at intervals during their lifetime, will eliminate altered cells in their precancerous stages and reduce the chance of overt cancers appearing later in life.

It has been established that inulin, when administered in its insoluble or particulate form, especially in the gamma polymorphic form as described above, is a potent APC activator and has a significant antitumour effect in mice.

Standards for (dissolved) "inulin for injection" are given in the British and U.S. Pharmacopoeias. Dissolved inulin and probably its hydrolysis products are excreted with a half-time of one hour in humans; the ultimate products of hydrolysis (fructose and glucose) are simple food-stuffs. The British Pharmaceutical Codex (1979) states that the only pharmacological effect of (dissolved) inulin is an osmotic diuresis at higher doses. Thus the only effect of particulate inulin, if any, should be related to its physical state. No nephrotoxicity or antigenic effects have been found in rabbits given a massive i.v. course of particulate inulin, and the only reported immunological interaction besides APC activation has been some cross-reaction with certain myeloma proteins derived from previously experienced bacterial levans. It should be noted that no attempts appear to have been made to purify or to define the physical forms of the inulin used.

In work leading to the present invention, it has been found that high purity inulin, when administered in its insoluble or particulate form, even at low dose rates, is a potent activator of the APC in vitro in mouse or human serum, the order of activity being similar to the most powerful activators known. The classical pathway of complement is unaffected. It has also been found that insoluble or particulate inulin has a potent anti-tumour effect on B-16 melanoma cells when given i.p. to C57 black mice, which display a 55% increase in mean survival time.

Accordingly, the present invention provides in a further aspect an immunotherapeutic preparation for activation of the alternative pathway of complement, or for antitumour treatment, which comprises as the active component thereof, particles of inulin or an inulin derivative in the gamma polymorphic form, characterised in that said active component has a low rate of solution in aqueous media above 30° C.

In a further aspect, the present invention extends to the use of an immunotherapeutic composition a broadly outlined above for the activation of the alternative pathway of complement in the human or animal body, or for antitumour treatment in the human or animal body.

Preferably, the active component is gamma inulin as characterised above.

The administration of an immunotherapeutic preparation as described above may be performed by any convenient means, for example by intraperitoneal, subcutaneous, intravenous or intra-tumour injection.

Of the three polymorphic forms of inulin now known—alpha, beta and gamma—it is preferable, in the present invention, to employ substantially pure gamma inulin having a molecular weight of at least 8000—more preferably 9000 to 12000—and formulated in an injectable preparation. The gamma form is preferred because it has been found that the ability of inulin to activate the APC and its anti-tumour effect is correlated with its insolubility, and the gamma form is the most insoluble and thus the most active. Further, dissolved inulin and polymorphic forms capable of dissolving substantially at 37° C. can interfere with these activities, and accordingly it is preferred that the suspension of inulin be free of the alpha and beta polymeric forms.

Gamma inulin for injection is preferably formulated as a sterile, milky suspension comprising 30–60 mg, preferably 50 mg, of pure, insoluble inulin particles per ml of saline, largely free of dissolved inulin and of endotoxin (less than 0.1 ng/ml by limulus amoebocyte lysate assay). Such a preparation has a significant but very low intrinsic pyrogenic effect, but passes the British Pharmacopoeia (1980) test for pyrogens at a dose of 10 mg/kg. It is expected to be free from traces of protein, lipid, nucleic acid and charged polysaccharides, and from soluble materials other than inulin or inulin hydrolysis products. The suspension is stable in the temperature range of, for example, from 0° C. to +45° C. and is preferably stored at 2°–8° C. as an aqueous suspension from which it slowly settles. A preservative such as phenyl mercuric nitrate (British Pharmacopoeia, 1980), for example at 20 $\mu$g/ml, may be included in the suspension without loss of in vivo or in vitro activity. The suspension is easy to handle and to inject, but must not be frozen or heated over 45° C. The particles may be prepared as ovoids less than 1 micron in diameter and do not tend to aggregate, and thus should not block microvasculature.

Further details of the preparation and use of the active components of the present invention are given in the following Example. In this description, all temperatures are in degrees Centigrade, and technical terms and abbreviations have the usual meaning in the art. Crude reagents, products and preparations can be purified by the means described herein, or by other means known in the art.

EXAMPLE 1

Inulin preparations a Inulin (90% w/w, Sigma, St.Louis, Miss., from dahlia tubers) was processed aseptically; final solutions were sterilized by membrane filtration. Dry weight was by refractive index at 26° C. All air-dried preparations contained ~10% $H_2O$ (w/w) and were polymers of fructose free of monomer [by reaction with Fehling's solution and mobility in ascending paper chromatography after but not before brief boiling in 2M trifluoroacetic acid, using the $AgNO_3$ (Trevelyan W. E., et.al., (1950) *Nature*, Lond. 166, pp.444–445) and resorcinol (Phelps, C. F. (1965) *Biochem. J.*, 95, pp.41–47) sprays]. Major and minor contents of fructose and glucose, respectively, were confirmed in all preparations using chromatography in chloroform:acetic acid:$H_2O$ (6:6:1) and water-saturated phenol after hydrolysis. Other reducing sugars were undetectable (<1%). All preparations were free of N and S, and C and H contents and specific rotations were as expected.

b. Inulin I. Crude inulin was stirred and washed twice at 23° C. with 0.1% (v/v) ammonia in deionized water (40 ml/g inulin); ~80% was insoluble.

c. Inulin II. Inulin I, dissolved in 0.1% ammonia (5 ml/g inulin, 69° C.) was slurried with 1% (w/w) DEAE cellulose (Eastman Kodak, Rochester, N.Y.) prepared for chromatography (Himmelhoch, S. R. (1971) in *Methods in Enzymology*, (Edited by Jakoby, W. B.), Vol.22, pp.273, Academic Press, New York), and the frozen filtrate was then allowed to stand (23° C., 48 hr), the filtered cake washed (5° C., 0.1% ammonia then dry acetone) and air-dried (yield 65–70%). Inulin II was the starting point for preparations described herein. Phenol-water chromatography after hydrolysis allowed elution and assay by the phenol-sulphuric method (Dubois, M. et. al. (1956), *Analyt. Chem.*, 28, 350–356), giving a fructose:glucose ratio of 20–80:1, consistent with a glucose terminal on the mol.wt. range described. Ash, P and O.D. (260 nm) were absent (crude inulin contained 0.6% w/w, 0.08% w/w and trace, respectively). Acetone washes contained no lipid. Titration of inulin II (10% w/v, pH 6.7, 20° C.) with N/100 HCl failed to detect carboxyl groups. Zero ash, and N after crystallisation from 0.1% ammonia, indicated zero anionic groups, and with zero S and P showed that ionizable contaminants were undetectable. O.D. scans (62.5 mg/ml) showed no peaks from 700–240 nm, provided that caramelization was avoided. The particles from aqueous crystallisation are smaller with more rapid crystallisation, as induced at higher concentration and pH, lower temperature and ionic strength, and by colloidal seeding.

d. ET-free gamma inulin for injection. Batches of different original alpha, beta and gamma content can be used, provided that sufficient molecules are >8000 mol.wt. Hardware should be pre-soaked in alkaline detergent (Decon 90, 5% v/v; Selby, Sydney); glassware should also be baked (3 hr, 195° C.) then assembled with oven-labile materials and autoclaved (Weinberg, 1981). Water is deionized by Milli-RO Reverse Osmosis then "polished" by Milli-Q filtration (Millipore, Sydney) and is then ET-free (Limulus assay). Water or solutions should be additionally treated to remove ET by filtration through sterile 0.2 $\mu$m Zetapor SP grade charge-modified nylon 66 membranes (AMF Cuno, Meriden, Conn.), and then autoclaved.

Crude inulin was dissolved by stirring (40 g, 800 ml 0.1% ammonia, 75° C.), clarified hot (Whatman No.42 paper), frozen (−15° C.) and then allowed to stand with 1 ml $CHCl_3$ (37° C., 3–4 days). The precipitate was washed twice (800 ml water, 23° C.), dissolved in recently boiled water (pH 6.5–7, 250 ml, 75° C.), and filtered slowly at 5–6% w/v and <40° C. through a 7 cm diameter, 2 cm deep bed of washed DEAE-cellulose. The filtrate (made 0.1% ammonia and 70° C.) was filtered through a similar bed of Amberlite sulphonic acid resin (CG-120, BDH, Poole, adjusted to the ammonium form), reheated with more ammonia (0.1%, 70° C.) then filtered (Zetapor).

The sterile, ET-free solution (pH 9–10, 5% w/v) was stirred (5° C., 5–7 days); if too large, the crystals should be redissolved with more ammonia (to 0.2%) and briefly heated to faint turbidity, which then provides seeding nuclei, then re-stirred (5° C., 3–5 days then 37° C., 2–4 days). The particles (90–99% gamma inulin) were centrifuged (30 min, 4000 g), resuspended by shaking (400 ml water, 50° C.) then heated (1 hr, 50° C.) and washed twice (5° C.). Yields are 40–50% but depend on mol.wt. of the starting material. The final suspension at 62.5 mg/ml was checked for dissolved matter (<0.2% w/v), particle size (see below), insolubility (<10% drop in O.D. at <1 mg/ml, 37° C., 24 hr), ET content (Limulus assay, "E-toxate", Sigma) and sterility at 23° and 37° C. It was stored at 2°–8° C. (although nothing dissolves after 18 days at 37° C., by refractive index); it must not be frozen or heated above 45° C. No aggregation will occur if unfrozen. The undiluted suspension settled very little and resuspended easily. Gamma inulin for injection is a sterile, ET-free (<6 pg ET/mg) suspension of 50 mg finely dispersed, insoluble gamma inulin per ml of 0.8% NaCl containing 20 µg/ml phenyl-mercuric nitrate, PMN [Fluka, Buchs, Switzerland, recrystallised (British Pharmacopoeia, 1980) and Zetapor-filtered] to facilitate multiple entry. Gamma inulin (50 mg/ml) had no effect on the antibacterial action of PMN. The suspension is stable for at least 22 months at 5° C.

e. Characterisation of gamma inulin. Electron micrographs (phosphotungstate stain) of gamma inulin for injection revealed ovoids of 0.7–1.4 µm diameter.

Molecular weight determinations were performed on gel chromatography columns on PBS. Calibration of a Biogel P-30 column with standard polysaccharide markers showed a peak of 8,500–10,000 (median ~9300) mol.wt. for gamma inulin, equivalent to 52–65 hexoses. Gamma inulin on a Sephadex G-50 column had a mol.wt. of ~300.

f. Solubility forms of inulin. Difficulties arising from the instability of the polymorphic forms of inulin were resolved by following decreases in turbidity (O.D., 700 nm) of <1 mg/ml finely divided inulin suspensions in cuvettes at 37° C., as some measure of their solution rate in vivo. They were resuspended by pi-petting, then stood briefly before reading in the spectrophotometer. The turbidity curves of different preparations were then found to change in a consistent manner as shown in FIG. 1.

The turbidity changes were reproducible and clear-cut and provided a convenient monitor to identify at least the following solubility forms (for "alpha" and "beta" nomenclature, see McDonald, E. J., (1946), Adv. Carbohyd. Chem., 2, 253–277).

1. beta $23^0$ inulin (very rapidly soluble at 23° C.);
2. beta $37^0$ inulin (soluble slowly at 23° C. but very rapidly at 37° C.);
3, 4 and 5. alpha $37^2$, alpha $37^8$ and alpha $37^{15}$ inulin (respectively soluble with half-times to reaching a plateau of turbidity of 2–4, 8 and 15 min. at 37° C.);
6. gamma inulin (slightly or undetectably soluble at 37° C.).

g. Toxicity of gamma inulin. A group of 5 mice accepted a course of 3 doses of 25 mg of purified gamma inulin over a period of 9 days without evident distress (total dosage 2.5 g/kg), but on sacrifice at day 10 their livers and spleens were found to be enlarged. Intravenous administration at 25 mg/kg caused collapse of the animals in 15–20 min followed by complete recovery, and the $LD_{50}$ by this route in mice was about 100 mg/kg.

EXAMPLE 2 a. Assays for APC activation

The assays depend on the known ability of the APC in mouse or human serum diluted in EGTA/$Mg^{2+}$ buffer to specifically lyse rabbit red blood cells (RBC). Activation of the APC develops labile reactive intermediates which rapidly decay. APC 'activators' thus destroy the APC in the serum, which then becomes unable to lyse rabbit RBC added subsequently. The amount of lost lytic activity is a measure of the amount of activation. Full details of these assays are ser out in Cooper, P. D. and Carter, M. (1986) *Molecular Immunology*, 23, 8, 895–901 and 903–908, incorporated herein by reference.

1. In vitro activation

Standardised portions of a serum diluted in EGTA/$Mg^{2+}$ buffer are incubated for 30 min. at 37° with graded doses of an activator suspension. The activator is then removed by centrifugation and standard portions of the supernatant are reincubated at 37° for a standard time with a known number of washed rabbit RBC. The amount of activation is measured as the proportion of unlysed cells quantitated by optical density at 640 nm.

2. In vivo activation

Graded doses of gamma inulin are inoculated i.p. into groups of three or four mice per time point, and the mice killed after various times, blood collected and serum pooled. Care is taken, using known procedures, to conserve complement activity. Standard portions of a series of dilutions in EGTA/$Mg^{2+}$ buffer of these sera, in comparison with similar dilutions of a contemporary pooled serum from untreated mice of the same batch, are incubated at 37° for a standard time with a calibrated number of washed rabbit RBCs. The amount of activation is measured as the proportion of unlysed cells quantitated by optical density at 640 nm.

b. Antitumour activity. Full details of antitumour activity of gamma.inulin in mice are set out in Cooper, P. D. and Carter, M. (1986) *Molecular Immunology*, 23 8, 903–908, incorporated herein by reference.

Mouse melanoma cells were grown in DMEM medium supplemented with 5% foetal bovine serum (both from Gibco, Paisley, Scotland). Cultures were split 1:8 every 7 days, yielding $1-1.5 \times 10^7$ cells per 75-$cm^2$ flask, and the mice were inoculated i.p. with $1 \times 10^6$ freshly harvested cells in 0.2 ml PBS, as previously described (Cooper, P. D. and Masinello, G. R., *Int.J.Cancer*, 32, 737–744 (1983)). All preparations were administered i.p., and there was no sign of distress in the animals after any dose. The survival times of individual mice were recorded daily and the significance of differences in mean survival time calculated by Student's t-test. All the mice were sex- and age-matched C57BL/6J; test samples comprised seven mice each and controls 14 or 21 mice each.

RESULTS a. APC Activation

It was found that gamma inulin is a potent activator of the APC in vitro in mouse or human serum at 2–8 µg/ml. This is an order of activity similar to the most powerful activators known.

FIG. 2a, left, compares in simultaneous tests the in vitro activation of the APC in human serum by gamma inulin with two other well-known activators, zymosan and SAC (Staphylococcus aureus Cowan type I, heat killed suspension). In these tests, a high unlysed RBC value indicates a high degree of APC activation in the serum.

FIG. 2b, right, compares the APC activation ability in human serum of the several forms of inulin, using the s=me method. Mouse serum gave almost identical results.

When given i.p. in mice, a minimum dose of 50 µg inulin (2.5 mg/Kg) produced detectable in vivo APC activation in the serum when serum is collected 2–16 hr after injection of the inulin (FIGS. 3a–g). This is a concentration comparable to the minimum dose for in vitro APC activation by inulin (FIG. 2).

The classical pathway of complement was unaffected.

b. Anti-tumour activity

Figure 4:
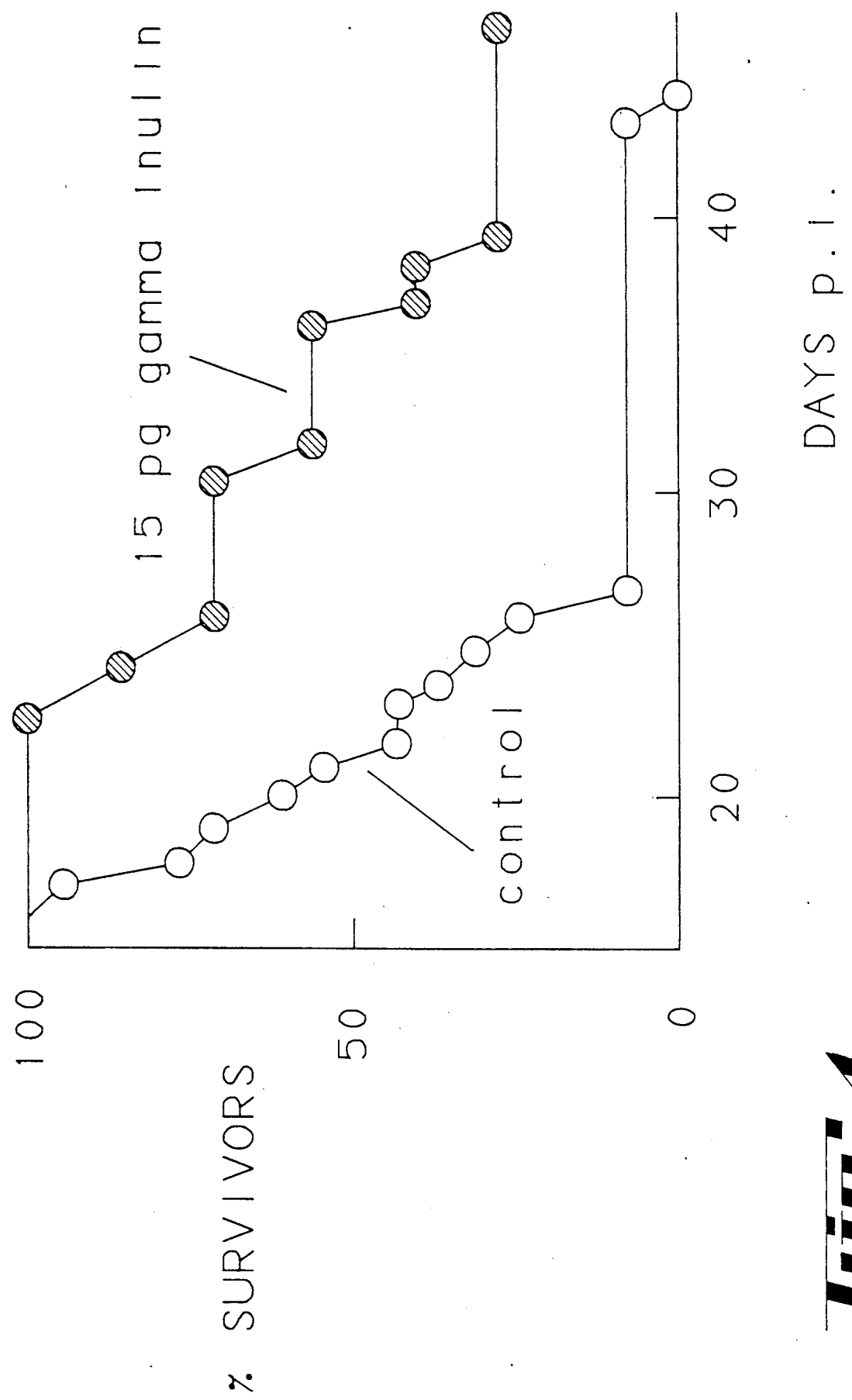

FIG. 4 depicts curves illustrating the increased survival time after gamma inulin treatment of C57 black mice inoculated i.p. on day 0 with B16 melanoma cells. The mice were given 15 µg of gamma inulin i.p. on day 1 and again on day 4 post-inoculation (p.i.)

DISCUSSION

It has been shown that gamma inulin has a potent anti-tumour effect on B16 melanoma cells. Treated mice displayed a 55% increase in mean survival time with doses as low as 1 mg/kg. Thus the lowest doses giving APC activation in vitro and in vivo are closely correlated with the minimal effective anti-tumour dose. The effect is not lost at doses as high as 5 mg/mouse (250 mg/kg). The more rapidly soluble forms of inulin (alpha and beta) are almost as active, but in these cases the action is blocked at higher doses. When inulin is dissolved by brief heating at 60°–70° its in vitro APC activation and its in vivo anti-tumour effect are simultaneously lost, but are regained on recrystallisation at lower temperatures. This effect, and its low dose requirement together with its high purity, confirms that it is the particulate inulin which is the active constituent.

From what is currently known of non-specific active immunotherapy, the optimal administration of preparations of the present invention is likely to be as close to the tumour as possible, i.e. the intratumour plus intravenous routes, representing a combination of regional and systemic treatment. Intracavity routes (peritoneal or thoracic) are expected to be useful, especially for effusions, and translated within a few hours into an activation of the APC in the blood. Intramuscular, subcutaneous and intradermal inoculations are likely to have a moderate "depot" effect and will be particularly useful to treat affected lymph nodes as the gamma inulin will tend to drain into them. Granuloma formation has not been seen in mice, cats or dogs by these routes. Orally, inulin will probably be digested but may be usefully passed to the intestinal mucosa by a delayed-release formulation. Topical application is expected to be effective. Sensitive tumour types are unknown, but those directly accessible to contact with inulin, e.g. in the blood, or with good blood supply, should be more susceptible. It is expected that the patient should be immunocompetent, and thus its most likely use as an adjunctive treatment will have to be carefully evaluated in terms of the cytotoxic or irradiation regimens included. Before timing and dosage can be determined, the maximum safe degree of activation of the APC in humans has to be ascertained. Such activation will probably have to be repeated as frequently as is allowed by the natural regeneration of the alternative pathway, which probably returns to normal levels in 24–48 hr. Initially, it is suggested that the following dose regimens might be effective—5–50 mg per adult human every 14 days, about half i.v. or s.c. and half intratumour (for comparison, the usual dose of dissolved inulin is 3 g i.v. initially, plus 7 g over the next few hours). It is likely, from rates of APC activation tolerated by renal dialysis patients, that the total dose of gamma inulin to be given intravenously will be given quite slowly, say 5 mg/10 minutes, perhaps by infusion in diluted form or by a micropump.

The degree of APC activation should be monitored carefully by in vitro tests, and the dose of inulin increased until detectable but subtoxic APC activation is observed. It is desirable also to follow a variety of other immunological parameters, such as macrophage, T and B cell activation, and natural killer cell activity.

The main side effect to be expected in humans is from direct, acute activation of the alternative pathway, mainly via the anaphylatoxins C3a and C5a. Mice happen to be very resistant to shock from this source. If C5a exceeds a certain blood level in humans the outcome appears to be irreversible, and there are other undesirable effects, e.g. from granulocyte emboli. One study with dissolved inulin in humans showed that 10–14 per cent APC activation passed without clinical remark, but another showed in haemodialysis patients that production by the dialysis membranes of greater than 8.5 µg/ml of the activation product C3a desArg produced undesirable clinical symptoms.

It is envisaged that gamma inulin may be usefully applied to internal or external body surfaces, where the inulin particles may pass into the body's circulation. Alternatively the gamma inulin, present in an external wound or on internal moist surfaces, may activate leukocytes which are then likely to migrate into the body to exert their immune influence. For these purposes gamma inulin may be applied topically to the skin or, in a suitable delayed-release vehicle, pass through the stomach to be liberated on intestinal mucosa or, in other vehicles such as suppositories, drops or aerosols, be inserted into the rectum, vagina, nose, throat, eyes or upper and lower respiratory tracts.

Gamma inulin is stable at room temperature and may be supplied in the usual pharamceutically acceptable formulations, vehicles and preparations, namely dried powders or suspensions in distilled water, saline or isotonic solutions, with or without preservatives. It may easily be sterilised by filtration and made into an injectable preparation free from endotoxin.

Gamma inulin, being inexpensively available, is as suitable for veterinary as for human applications.

The action of gamma inulin represents a single, clean signal to the immune system, namely the activation of the alternative pathway of complement (APC). The purity of this signal is important in allowing the elimination of undesirable side effects. However, the immune system is extremely complex and usually responds in nature to a number of different immune signals from stimulating entities (for example, a noxious microbe or parasite, a cancer cell, a vaccinating antigen or an allergenic substance, among others). It is by the interaction of such signals that the body achieves its powerful response to a very large variety of "foreign" stimuli. It is therefore natural to expect that gamma inulin will achieve its most potent effect in synergistic action with other immune-stimulating signals.

An important application for gamma inulin is as an enhancer or immune adjuvant to a vaccinating antigen or to substances that immunologically mimic the three-dimensional structure of the antigen's reactive region (its epitope). These substances are often poorly antigenic on their own. They may comprise carefully designed peptide sequences or may be antiidiotype immuno globulins. The latter have as their eliciting antigen the idiotype (region binding to an epitope) of those immune globulins elicited by the original antigen. The antiidiotype, by being complementary to a structure itself complementary to the original antigen, thus resembles that antigen in its three-dimensional structure.

Gamma inulin has been found to have vaccine adjuvant activity. As an example of this, an antigen (either bovine serum albumin or keyhole limpet haemocyanin) inoculated into mice elicited substantially more antibody if given as a mixture with gamma inulin than if given on its own. Groups of mice were injected with each preparation and the mean antibody concentrations measured in micrograms/ml by radioimmune or ELISA assays. In one test, the antibody concentration elicited by the mixture of gamma inulin and antigen was 6.2 times that elicited by the antigen alone ($p<0.001$), while the antibody elicited by the antigen in an emulsion with Freund's Complete Adjuvant (a known, powerful adjuvant that is too toxic for human application) was 10.4 times that of the antigen alone ($p<0.001$).

Other immune modulators that are likely to act synergistically with gamma inulin are:
a. the interleukins, the interferons, the tumour necrosis factors and many other identified immune stimulatory factors that are collectively known as lymphokines or cytokines;
b. thymocyte stimulators such as levamisole, or the several thymus stimulating hormones, one of which is thymosin;
c. macrophage stimulators such as the muramyl peptides or other microbial components;
d. endotoxin;
e. whole microbes.

By way of example of such synergism, it was found that a mixture of crude interferon and crude tumour necrosis factor, injected with gamma inulin into mice previously inoculated with the B16 melanoma, gave a mean survival time >30% greater than either gamma inulin or the lymphokine mixture on their own, neither of which produced any survivors. More importantly, gamma inulin plus the lymphokines eliminated the tumour entirely from ca. 30% of the mice, a finding rarely made in this system. Similar results are obtained with the thymocyte stimulator succinyl concanavalin A.

An immune stimulator such as gamma inulin is likely to have a beneficial effect on any human or animal disorder with an immunological component. Cancer cells can be recognised by the immune system as foreign to the body, or "nonself". The beneficial effect of gamma inulin on cancer in a mouse model has been demonstrated above, and this benefit, with or without synergistic action of other immune modulators, is likely to extend to human or animal cancer patients.

An extension of this benefit is as follows. The carcinogenic process, whereby a normal cell is changed to a fully malignant cell, is known to occupy many years in man. During this process, of which the eventual victim is usually unaware, the damaged cell multiplies slowly and passes through several stages in which its progeny are not yet fully malignant but nevertheless may be recognised by the immune system as abnormal or nonself. This would require a boosting immune stimulus in those cases otherwise destined to escape detection by the body's immune defences. Consequently a treatment during the carcinogenic process with an immune stimulator with negligible side effects, such as gamma inulin, is likely to eliminate the premalignant cells and lessen the chance of later emergence of fully malignant progeny cells. Thus regular treatment with gamma inulin, with or without other immune modulators and at say three year intervals, of persons at risk (for example those over 40 years of age and/or those with identifiable high risk factors) is likely to decrease the overall incidence of malignant disease in the community.

Infections with microbes, worms or parasites, particularly those of a more chronic course, are likely to be combatted by appropriate treatment with gamma inulin, with or without other immune modulators. Other immune disorders such as allergic or rheumatic diseases, immune deficiency diseases, or neurological or gastrointestinal disorders related to dysfunction of the immune system, ar likely to be similarly responsive.

Those skilled in the art will appreciate that modifications and variations to the invention described above are possible without departing from the present inventive concept.

I claim:

1. A composition comprising particles of inulin, wherein said particles are in the gamma polymorphic form and are virtually insoluble in aqueous media at 37° C.

2. A composition according to claim 1, wherein said inulin has a molecular weight greater than 8,000.

3. A composition according to claim 1, comprising particles of gamma inulin, wherein the gamma inulin has a molecular weight in the range of from about 8,000 to about 16,000 and is virtually insoluble in water at 37° C.

4. A composition according to claim 3, wherein said gamma inulin is in the form of a stable pure suspension of particles <1 μm in diameter.

5. An immunotherapeutic preparation for activation of the alternate pathway of complement (APC) in a human or animal body, which comprises as the active component thereof particles of inulin in the gamma polymorphic form, wherein said particles are virtually insoluble in aqueous media at 37° C.; and a pharmaceutically acceptable diluent or carrier.

6. A preparation according to claim 5, wherein said active component comprises particles of gamma inulin.

7. A preparation according to claim 5, wherein said carrier or diluent is a sterile, aqueous vehicle.

8. A preparation according to claim 7, wherein said aqueous vehicle is an isotonic solution.

9. A preparation according to claim 5 in a form suitable for injection.

10. A preparation according to claim 5 in a form suitable for oral, rectal, vaginal, topical, nasal or ocular administration.

11. A preparation according to claim 5, further comprising a second active component which is an immune modulator.

12. A preparation according to claim 4, wherein said immune modulator is a vaccinating antigen, an antigenic peptide sequence, or an anti-iodiotype immune globulin.

13. A preparation according to claim 11, wherein said immune modulator is an interleukin or an interferon or tumor necrosis factor or other lymphokine, or thymocyte stimulator or other thymus stimulating hormone, a muramyl peptide or other microbial component or whole microbial component or whole microbe, or an endotoxin.

14. A method for the activation of the alternative pathway of complement (APC) in a human or animal body, which comprises administering to the human or animal body an effective amount for said activation of an immunotherapeutic preparation according to claim 5.

15. A method for enhancement of an immune response in a human or animal body to which has been administered an immune modulator which comprises administering to the human or animal body an effective amount for said enhancement of an immunotherapeutic preparation according to claim 5.

16. A method for enhancement of the effect of administration of a vaccinating antigen, an antigenic peptide sequence, or an anti-idiotype immune globulin, in a human or animal body which comprises administering as an adjuvant an effective amount for said enhancement of an immunotherapeutic preparation according to claim 5.